(12) United States Patent
Chi et al.

(10) Patent No.: US 6,773,896 B2
(45) Date of Patent: Aug. 10, 2004

(54) METHOD FOR DIRECT MEASUREMENT OF COAGULATION FACTOR VIIA ACTIVITY IN PLASMA

(75) Inventors: Liguo Chi, Ann Arbor, MI (US); Robert Joseph Leadley, Jr., Dexter, MI (US); Yun-Wen Peng, Ann Arbor, MI (US)

(73) Assignee: Warner-Lambert Company, Morris Plains, NJ (US)

(*) Notice: Subject to any disclaimer, the term of this patent is extended or adjusted under 35 U.S.C. 154(b) by 189 days.

(21) Appl. No.: 10/141,396

(22) Filed: May 8, 2002

(65) Prior Publication Data

US 2002/0168700 A1 Nov. 14, 2002

Related U.S. Application Data

(60) Provisional application No. 60/289,539, filed on May 8, 2001.

(51) Int. Cl.[7] ............................ C12Q 1/56; C12Q 1/00; G01N 33/53
(52) U.S. Cl. .............................. 435/13; 435/4; 435/968
(58) Field of Search .............................. 435/13, 4, 968

(56) References Cited

U.S. PATENT DOCUMENTS

| | | | |
|---|---|---|---|
| 5,399,487 A | 3/1995 | Butenas et al. | 435/13 |
| 5,472,850 A | 12/1995 | Morrissey | 435/13 |
| 5,741,658 A | 4/1998 | Morrissey | 435/23 |
| 5,750,358 A | 5/1998 | Morrissey | 435/13 |
| 6,100,050 A | 8/2000 | Hemker et al. | 435/13 |
| 2002/0168700 A1 * | 11/2002 | Chi et al. | 435/13 |

FOREIGN PATENT DOCUMENTS

| | | |
|---|---|---|
| EP | 0641443 | 10/1999 |
| EP | 2009326 | 11/2002 |
| WO | 9206711 | 4/1992 |
| WO | 9218870 | 10/1992 |
| WO | 9405328 | 3/1994 |
| WO | 9407515 | 4/1994 |
| WO | 9719357 | 5/1997 |
| WO | 9947699 | 9/1999 |
| WO | 0030646 | 6/2000 |

OTHER PUBLICATIONS

Sabharwal et al, J. of Biological Chemistry, V. 270(26), pp 15523–30, (Jun. 1995), (Abstract Only).*

Seligsohn et al., "Coupled Amidolytic Assay for Factor VII: Its Use With a Clotting Assay to Determine the Activity State of Factor VII", *Blood*, vol. 52, No. 5, 1978, pp. 978–988.

Kario et al., "The strong positive correlation between factor VII clotting activity using bovine thromboplastin and the activated factor VII level", *Thrombosis and haemostasis*, vol. 73, No. 3, 1995, pp. 429–434.

Jeske et al., "Measurement of functional and immunologic levels of tissue factor pathway inhibitor. Some methodologic considerations", *Blood coagulation & fibrinolysis*, 6 Suppl 1, 1995, pp. 573–580.

Hawthorne et al., "Isolation and characterization of recombinant anncain V expressed in Saccharortisyces cerevisine", *Journal of Biotechnology*, vol. 36, No. 2, 1994, pp. 129–143.

(List continued on next page.)

*Primary Examiner*—Louise N. Leary
(74) *Attorney, Agent, or Firm*—Andrew J. Leon; Cynthia M. Bott (57) ABSTRACT

The present invention generally provides a method of measuring the biological activity of Coagulation Factor VIIa (Factor VIIa). Specifically, the present invention provides a method for directly measuring the activity of Factor VIIa in a plasma sample. More specifically, the present invention provides a method for utilizing Factor VIIa activity as a bio-marker to monitor Factor VIIa inhibition to screen compounds which are able to inhibit the biological activity of Factor VIIa.

22 Claims, 7 Drawing Sheets

OTHER PUBLICATIONS

Chabbat et al., "Aprotinin is a competitive inhibitor of the factor VIIa–tissue factor complex", *Thrombosis Research*, vol. 73, No. 3, 1993, pp. 205–215.

Sandset et al., "Chromogenic substrate assay of extrinsic pathway inhibitor (EPI): levels in the normal population and relation to cholesterol", *Blood coagulation & fibrinolysis*, vol. 2, No. 3, 1991, pp. 425–433.

Kumar et al., "Identification of molecular sites on factor VII which mediate its assembly and function in the extrinsic pathway activation complex", *Journal of Biological Chemistry*, vol. 266, No. 2, 1991, pp. 915–921.

Abildgaard et al., "The inhibitor of F VIIa in plasma measured with a sensitive chromogenic substrate assay: comparison with antithrombin, protein C and heparin cofactor II in a clinical material", *Folis haematologica; internationals Magazin fur klinische und morpbologische Flutforschung*, vol. 115, No. 3, 1988, pp. 274–277.

Sndset et al., "Heparin induces release of extrinsic coagulation pathway inhibitor (EPI)", *Thrombosis Research*, vol. 50, No. 60, 1988, pp. 803–813.

Oliver et al., "Active site–inhibited coagulation factor VIIa blocks platelet activation, thrombin generation, and accumulation of platelet–bound factor X in a tissue factor–initiated system", *Blood*, vol. 86, No. 10, Suppl. 1, 77A, 1995.

Fareed et al., "Effect of Recombinant Hirudin and Heparin on the Functional and Immunologic Levels of TFPI, Results of Experimental and Clinical Studies", *Blood*, vol. 82, No. 10, Suppl. 1, 616a, 1993.

Peterson et al., "Thermal effects on an enzymatically latent conformation of coagulation factor VIIa", *European Journal of Biochemistry*, vol. 261, No. 1, 1999, pp. 124–129.

Neuenschwander and Morrissey, "Roles of the membrane–interactive regions of factor VIIa and tissue factor. The factor VIIa GIa domain is dispensable for binding to tissue factor but important for activation of factor X", *Journal of Biological Chemistry*, vol. 269, No. 11, 1994, pp. 8007–8013.

Wildgoose et al., "Identification of calcium binding site in the protease domain of human blood coagulation factor VII: evidence for its role in factor VII–tissue factor interaction", *Biochemistry*, vol. 32, No. 1, 1993. pp. 114–119.

Ruf et al., "Cofactor residues lysine 165 and 166 are critical for protein substrate recognition by the tissue factor–factor VIIa protease complex", *Journal of Biological Chemistry*, vol. 267, No. 9, 1992, pp. 6375–6381.

Ieko et al., "The influence of beta2–glycoprotein 1 on tissue factor activity", *Seminars in Thrombosis and Hemostasis*, vol. 24, No. 3, 1998, pp. 211–215.

Fiore et al., "An unusual antibody that blocks tissue factor/factor VIIa function by inhibiting cleavage only of macromolecular substrates", *Blood*, vol. 80, No. 12, 1992, pp. 3127–3134.

Kam et al., "Thioester thromogenic substrates for human factor VIIa: Substituted isocoumarins are inhibitors of factor VIIa and in vitro anticoagulants", *Thrombosis and Haemostatis*, vol. 64, No. 1, 1990, pp. 133–137.

Sandset et al., "A sensitive assay of extrinsic coagulation pathway inhibitor (EPI) in plasma and plasma fractions", *Thrombosis Research*, vol. 47, No. 4, 1987, pp. 389–400.

Baughman and Lytwyn, "Effect of sera on thrombin activation rate constants: A one–stage assay of the extrinsic system", *Annals of the New York Academy of Sciences*, vol. 370, 1981, pp. 822–835.

Tubbs et al., "Procoagulant Activities of Factor VIIa in Haemophilic Plasma", *Br. J. Haematol.*, vol. 76, Suppl. 1, 1990, p. 33.

Petersen Lars C et al: "Thermal effects on an enzymatically latent conformation of coagulation factor VIIa," European Journal of Biochemistry, vol. 261, No. 1, Apr. 1999, pp. 124–129, XP0002216886 ISSN: 0014–2956.

Morrissey James H et al: "Quantitation of activated factor VII levels in plasma using a tissue factor mutant selectively deficient in promoting factor VII activation." Blood, vol. 81, No. 3, 1993, pp. 734–744, XP002216887 ISSN: 0006–4971.

Kario Kazuomi et al: "Fluorogenic assay of activated factor VII: Plasma factor VIIa levels in relatin to arterial cardiovascular diseases in Japanese." Artheriosclerosis and Thrombosis, vo. 14, No. 2, 1994, pp. 265–274, XP002216888.

* cited by examiner

METHOD FOR DIRECT MEASUREMENT OF COAGULATION FACTOR VIIA ACTIVITY IN PLASMA

CROSS REFERENCE TO RELATED APPLICATIONS

This application claims benefit of priority from U.S. Provisional Application No. 60/289,529, filed May 8, 2001.

FIELD OF THE INVENTION

The present invention generally provides a method of measuring the biological activity of Coagulation Factor VIIa (Factor VIIa). Specifically, the present invention provides a method for directly measuring the activity of Factor VIIa in a plasma sample. More specifically, the present invention provides a method for utilizing Factor VIIa activity as a bio-marker to monitor Factor VIIa inhibition to screen compounds which are able to inhibit the biological activity of Factor VIIa.

BACKGROUND OF THE INVENTION

In the coagulation cascade, Factor VII plays an important role in clot formation. Factor VII is activated by tissue factor (TF) to form Factor VIIa. As one of its functions, Factor VIIa catalyzes the activation of Factor X to Factor Xa which leads to clot formation.

The TF/VIIa complex is thought to play a key role in thrombogenesis in patients with acute coronary syndromes. Therefore, Factor VIIa is an attractive target for antithrombotic therapy. Because Factor VIIa inhibitors are attractive therapeutic agents, a number of such compounds are under scientific evaluation in clinical development.

Methods for detecting the bioactivity of Factor VIIa inhibitors in plasma are essential for identifying and developing Factor VIIa inhibitors. Prior art methods for measuring Factor VIIa in plasma include the use of truncated tissue factor agents as disclosed in U.S. Pat. Nos. 5,472,850; 5,741,658 or indirect, 2-stage assays which are based on the conversion of Factor X to Factor Xa as catalyzed by Factor VII to provide an indirect measure of Factor VIIa activity and are disclosed in the COASET® method (Chromogenix AB, Mölndal, Sweden). Since the COASET® method involves the cleavage of a Factor Xa chromogenic substrate following the activation of Factor X, this method does not provide a direct measure of Factor VIIa activity.

Accordingly, it would be both desirable and advantageous to have a plasma-based, direct (1-step) Factor VIa activity assay which can be utilized as an ex vivo plasma bio-marker assay for obtaining accurate Factor VII bioactivity measurements and also for use in screening compounds for their ability to inhibit Factor VIIa in vivo.

SUMMARY OF THE INVENTION

The present invention provides a method for directly measuring the activity of Coagulation Factor VIIa (Factor VIIa) in a plasma sample. The method comprises the step of combining a quantity of a plasma sample with a solution comprising a buffer, Factor VII, and a detectable Factor VIIa substrate, and then detecting the amount of the detectable substrate catalyzed to determine the activity of Factor VIIa in the sample.

The present invention also discloses a method for determining whether a compound is useful for inhibiting Factor VIIa biological activity.

DETAILED DESCRIPTION OF THE INVENTION

The present invention provides a method for measuring the activity of Factor VIIa in an assay which allows for directly measuring Factor VIIa activity in a plasma sample without the confounding influence of other factors in order to obtain the activity of Factor VIIa.

By "Factor VIa activity" is meant the cleavage of a Factor VIIa specific substrate.

As used herein, the term "inhibit" means a decrease in a function. Preferably, a compound that inhibits Factor VIIa does so by at least 10%, more preferably by at least 25%, and most preferably by at least 50% and can be defined as an "inhibitor" of Factor VIIa activity.

The term "subject" as used herein means all animals including mammals, such as humans. Examples of subjects include humans, rodents, and monkeys.

The method of the present invention generally includes the steps of combining a quantity of a plasma sample with acetonitrile ($CH_3CN$), drying the plasma sample, combining the dried plasma with a solution containing a buffer, Factor VIIa, and a detectable Factor VIIa substrate. The method further includes the step of detecting the amount of the detectable substrate catalyzed to determine the activity of Factor VIIa in a sample. The preferred substrates for the present invention include peptides having a paranitroaniline chromophore attached thereto. Examples of specific Factor VIIa substrates are available from SPECTROZYME® FVIIa (Cat #217, American Diagnostica Inc, Greenwich, Conn.).

Substrates can be labeled with other chromogenic compounds including fluorescein, tetramethyl rhodamine, coumarin, or biotin. Other suitable detectable labels known to those skilled in the art may be utilized in the method of the present invention. Preferably, the detectable labels include a chromophore which can be quantified utilizing well-known devices and techniques including the use of a spectrophotometer measuring absorbance at a predetermined or preselected wavelength. For the paranitroaniline labeled substrates used in the present invention, the chromophore is detectable by spectroscopy at 405 nm.

The buffer solution utilized is preferably a Tris buffer (comprised of 50 mM Tris, 100 mM NaCl, pH 7.4) contain 0.625% plasma, 0.1% bovine serum albumin (BSA), Factor VIIa (10 nM), tissue factor (TF) (15 nM), $CaCl_2$ (5 mM), and the Factor VIIa substrate (0.5 mM). Other buffers, such as HEPES, can also be utilized.

A further method is provided for determining whether a candidate compound inhibits Factor VIIa activity and includes the steps of administering to a subject a candidate compound, obtaining a plasma sample from the subject at a time period after the administration of the candidate compound, combining a portion of the plasma sample with acetonitrile, drying the plasma sample, combining the dried plasma sample with a solution comprising a buffer, Factor VIIa, TF, and a detectable Factor VIIa substrate. The method further includes the step of measuring Factor VIIa activity, wherein inhibited Factor VIIa activity relative to a control not contacted with the candidate compound indicates that the candidate compound inhibits Factor VIIa activity. That is, by measuring the amount of the detectable substrate catalyzed by Factor VIIa relative to the control, decreased substrate catalyzed relative to the control indicates that the candidate compound inhibits Factor VIIa and no change in substrate catalyzed relative to the control indicates that the candidate compound does not inhibit Factor VIIa.

The following examples further illustrate the present invention. These examples are intended merely to be illustrative of the present invention and are not to be construed as limiting.

EXAMPLE 1

The tissue factor (TF)/factor VIIa (FVIIa) complex plays a key role in thrombogenesis in patients with acute coronary syndromes. Thus, FVIIa has become an attractive antithrombotic therapeutic target. A number of FVIIa inhibitors have been under scientific evaluation and clinical development. However, there is no direct, specific assay currently available for measuring the bioactivity of FVIIa inhibitors in plasma. The commercially available COASET® Factor VII is a two-stage assay, which involves the cleavage of a FXa chromogenic substrate following the activation of FX. Thus, it is not a direct measure of FVIIa activity. Applicants have developed a new, plasma-based, direct (one-stage) FVIIa activity assay. This assay is based on the cleavage of a chromogenic FVIIa substrate (Spectrozyme FVIIa) by exogenously added human TF and FVIIa in plasma. The specificity and sensitivity of this new assay were validated by using thrombin, FXa, and FVIIa inhibitors in vitro. The utility of the assay as an ex vivo plasma bio-marker in rabbits treated with small molecule FVIIa inhibitors was also studied.

Methods

The following chemicals were used in this study: Tris acid (Gibco BRL); NaCl, bovine serum albumin (BSA), and $CaCl_2$ (Sigma); recombinant human tissue factor, human recombinant FVIIa, and spectrozyme FVIIa, $CH_3SO_2$—D—CHA—But—Arg—pNA.AcOH (American Diagnostica, Greenwich, Conn.); acetonitrile ($CH_3CN$) (J. T. Baker).

Blood Sampling and Plasma Preparation

Blood samples from rabbit (New Zealand White) and normal human volunteers were collected in tubes containing 3.8% sodium citrate (9 volumes of blood into 1 volume of sodium citrate). Blood was centrifuged at 2000 g for 10 minutes and plasma was stored at −70° C. until analyzed.

In Vitro Study

The proteolytic activity of FVIIa was measured by cleavage of paranitroanilide (pNA) substrate (Spectrozyme FVIIa) in a 96-well microtiter plate.

A series of samples containing enzyme inhibitors (0–300 $\mu$M) were added to well in a 96-well microtiter plate containing Tris-buffer (50 nM Tris, pH 7.4, 100 mM NaCl), 0.625% plasma, 0.1% BSA. After addition of FVIIa (10 nM in final concentration), the plate was incubated for 15 minutes at 37° C. Then the TF (15 nM in final concentration) and $CaCl_2$ (5 mM in final concentration) were added, and the plate was incubated for additional 15 minutes at 37° C. again. After incubation, the substrate (Spectrozyme FVIIa) was added at a final concentration of 0.5 mM to result in a final volume of 200 $\mu$L/well. The rate of change in absorbance at 405 nm was monitored by a Softmax plate reader (Molecular Devices).

Ex vivo study of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid in rabbit plasma The FVIIa activity was measured in the plasma collected from rabbits that received 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid, IV bolus, 3 mg/kg (n=3). Blood samples were collected before and 1, 5, 10, 30, and 60 minutes after the onset of administration, followed by plasma preparation. 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid in plasma was extracted using 4 volumes of $CH_3CN$ to 1 volume of plasma. Precipitated proteins were removed by centrifugation at 2000 g for 5 minutes. Solvent was decanted into small glass tubes and dried at 37° C. under a stream of nitrogen, then reconstituted in Tris-buffer. The method of FVIIa activity assay is the same as in vitro study. FVIIa activity was determined by measuring the rate of absorbance change at 405 nm due to cleavage of the spectrozyme FVIIa (0.5 mM) by FVIIa/TF complex. Plasma concentrations of 2-[6-(3-Carbamimidoyl-phenoxy)-3,5-difluoro-4-(1-methyl-3-phenyl-propylamino)-pyridin-2-yloxy]-5-dimethylamino-4-methyl-benzo acid were determined by using a standards inhibition curve that were generated from rabbit plasma containing known amount of inhibitor and processed identically to test samples.

Ex vivo study of 7-[(R)-3-(3-Amino-benzyl)-4-(4-amino-phenyl)-4-methyl-2,5-dioxo-imidazolidin-1-ylmethyl]-naphthalene-2-carboxamidine in hypercholesterolemic rabbit plasma The FVIIa activity was measured in plasma collected from hypercholesterolemic rabbits in a balloon-induced injury model of thrombosis. The rabbits received two doses of 7-[(R)-3-(3-Amino-benzyl)-4-(4-amino-phenyl)-4-methyl-2,5-dioxo-imidazolidin-1-ylmethyl]-naphthalene-2-carboxamidine, IV bolus, 0.3 mg/kg (n=5) and 1.0 mg/kg (n=6). Blood samples were collected before and 3 minutes after administration, followed by plasma preparation. Plasma samples were extracted using $CH_3CN$ and reconstituted in Tris-buffer. The protocol is the same as ex vivo study of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid. The plasma levels of 7-[(R)-3-(3-Amino-benzyl)-4-(4-amino-phenyl)-4-methyl-2,5-dioxo-imidazolidin-1-ylmethyl]-naphthalene-2-carboxamidine were calculated based on the test plasma FVIIa activity and an $IC_{50}$ standard curve. The standard curve was generated in vitro by using hypercholesterolemic rabbit plasma containing known amount of inhibitor and processed identically to test samples.

Results

In vitro inhibitory effects of FVIIai, 2-[6-(3-Carbamimidoyl-phenoxy)-3,5-difluoro-4-(1-methyl-3-phenyl-propylamino)-pyridin-2-yloxy]-5-dimethylamino-4-methyl-benzoic Acid, ({2-(5-Carbamimidoyl-2-hydroxy-phenoxy)-3,5-difluoro-6-[3-(1-methyl-4,5-dihydro-1H-imidazol-2-yl)-phenoxy]-pyridin-4-yl}-methyl-amino)-acetic Acid, and (S)-4-[3-(cyclopentylmethylamino)-2-[(2-naphthalenylsulfony)amino]-3-oxopropyl]-benzenecarboximidic acid hydrazide on FVIIa activity in human plasma Factor VIIai (an active site-inactivated FVIIa) which competes with physiologic FVIIa in the activation of FX, binds to tissue factor but is unable to initiate coagulation (P Golino, M. Ragni, P. Cirillo, et al., Antithrombotic effects of recombinant human, active site-blocked factor VIIa in a rabbit model of recurrent arterial thrombosis. *Circ. Res.*, 1998;82:39–46). 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid ($IC_{50}$=15 nM against human FVIIa) is a synthetic small molecular FVIIa inhibitor. ({2-(5-Carbamimidoyl-2-hydroxy-phenoxy)-3,5-difluoro-6-[3-(1-methyl-4,5-dihydro-1H-imidazol-2-yl)-phenoxy]-pyridin-4-yl}-methyl-amino)-acetic acid (Ki=0.11 nM against human FXa) is a small molecule, potent FXa inhibitor. (S)-4-[3-(Cyclopentylmethylamino)-2-[(2-naphthalenylsulfony)amino]-3-oxopropyl]benzenecarboximidic acid hydrazide (Ki=0.38 nM, $IC_{50}$=2 nM against thrombin) is a highly selective, potent, thrombin inhibitor.

Figure 1:
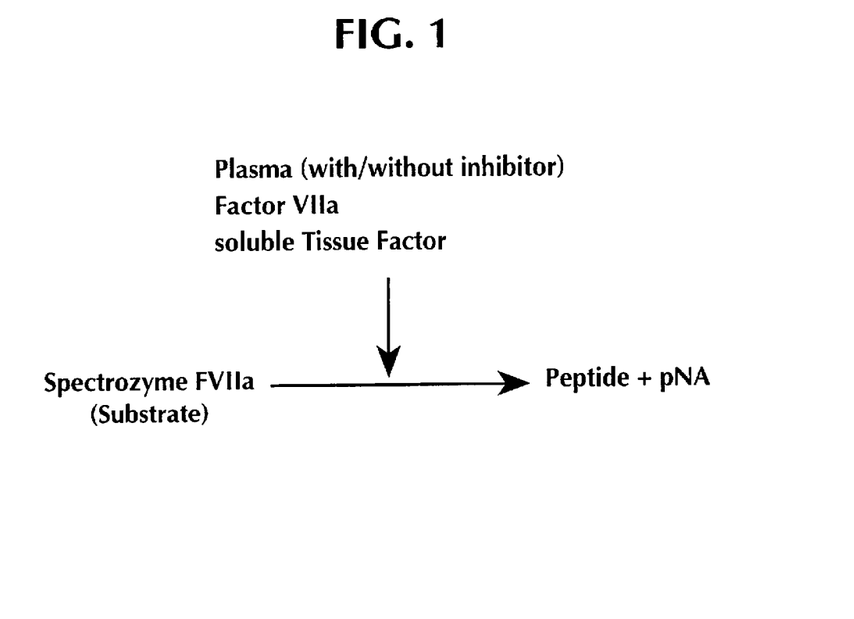
FIG. 1 shows a scheme for the 1-step Factor VIIa activity assay reaction.

Above four inhibitors were evaluated in pooled human plasma for their inhibitory effects on FVIIa activity. Effects of FVIIai, 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid, ({2-(5-Carbamimidoyl-2-hydroxy-phenoxy)-3,5-difluoro-6-[3-(1-methyl-4,5-dihydro-1H-imidazol-2-yl)-phenoxy]-pyridin-4-yl}-methyl-amino)-acetic acid, and (S)-4-[3-(cyclopentylmethylamino)-2-[(2-naphthalenylsulfony)amino]-3-oxopropyl]benzenecarboximidic acid hydrazide on FVIIa activity were compared with their own control group. The activity of FVIIa was obtained with a final concentration of 0.625% human plasma, 10 nM FVIIa, 15 nM TF, 5 mM $CaCl_2$, and 0.5 mM SPZFVIIa. As shown in FIG. 1, FVIIai (172 nM) and 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid (300 nM) significantly decreased FVIIa activity in human plasma. In contrast, ({2-(5-Carbamimidoyl-2-hydroxy-phenoxy)-3,5-difluoro-6-[3-(1-methyl-4,5-dihydro-1H-imidazol-2-yl)-phenoxy]-pyridin-4-yl}-methyl-amino)-acetic acid (100 nM) and (S)-4-[3-(cyclopentylmethylamino)-2-[(2-naphthalenylsulfony)-amino]-3-oxopropyl]benzenecarboximidic acid hydrazide (100 nM) did not alter FVIIa activity in the assay. The result indicated that this assay was relatively specific for FVIIa inhibitors, but not for FXa and thrombin inhibitor.

Figure 2:
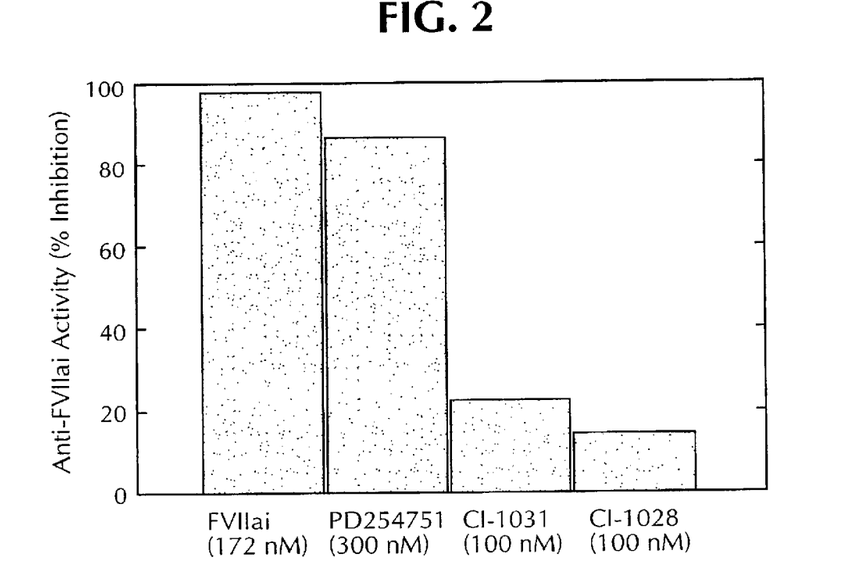
FIG. 2 shows the in vitro inhibitory effects of FVIIai, 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid (PD 254751), ({2-(5-Carbamimidoyl-2-hydroxy-phenoxy)-3,5-difluoro-6-[3-(1-methyl-4,5-dihydro-1H-imidazol-2-yl)-phenoxy]-pyridin-4-yl}-methyl-amino)-acetic acid (CI-1031), and (S)-4-[3-(cyclopentylmethylamino)-2-[(2-naphthalenylsulfonyl)amino]-3-oxoprpoyl]-benzenecarboximidic acid hydrazide (CI-1028) on factor VIIa activity in human plasma.

A series of concentration of FVIIai and 2-[6-(3-Carbamimidoyl-phenoxy)-3,5-difluoro-4-(1-methyl-3-phenyl-proplylamino)-pyridin-2-yloxy]-5-dimethylamino-4-methyl-benzoic acid were evaluated in human plasma for their inhibitory effects on FVIIa activity. FVIIai and 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid, the two FVIIa inhibitors, displayed a dose-dependent inhibition on FVIIa activity in human plasma (see FIG. 2).

Figure 3:
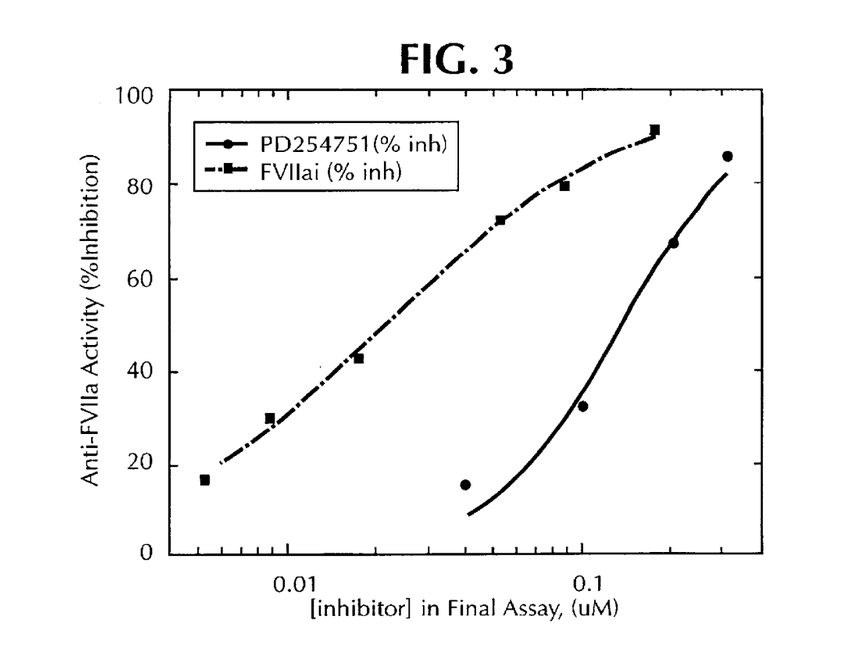
FIG. 3 is a graph showing the in vitro anti-FVIIa activity of FVIIai and 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid (PD 254751) in human plasma.

In vitro and ex vivo study of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid in rabbit plasma Defined concentrations of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid (0.01 to 3 $\mu$M) were added to Tris-buffer or normal rabbit plasma. The $IC_{50}$ standard curve was determined by means of assay from Tris-buffer or $CH^3CN$ extraction from plasma samples. FIG. 3 indicates that the $IC_{50}$ standard curves were not significantly different between $CH_3CN$ extracted sample and Tris-buffer. It shows that a good recovery of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid added to plasma by means of $CH_3CN$ extraction.

The plasma concentration of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid was calculated based on the measurement of FVIIa activity in the plasma by using the FVIIa activity assay. Plasma levels of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid were measured with reference to the $IC_{50}$ standard curve that was generated from rabbit plasma containing known amount of inhibitor and processed identically to test samples (n=3). There was a time-dependent change in plasma concentration of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid after an IV bolus administration (see FIG. 4).

Figure 5:
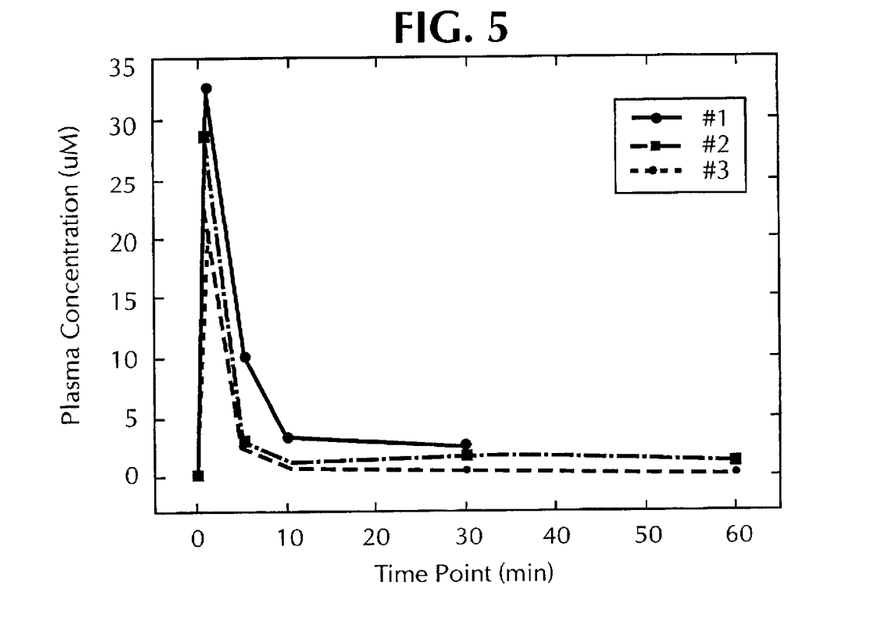
FIG. 5 is a graph showing the results of an ex vivo study of 2-[6-(3-Carbamimidoyl-phenoxy)-3,5-difluoro-4-(-methyl-3-phenyl-propylamino)-pyridin-2-yloxy]-5-dimethylamino-4-methyl-benzoic acid (PD 254751) in rabbit plasma.
Figure 6:
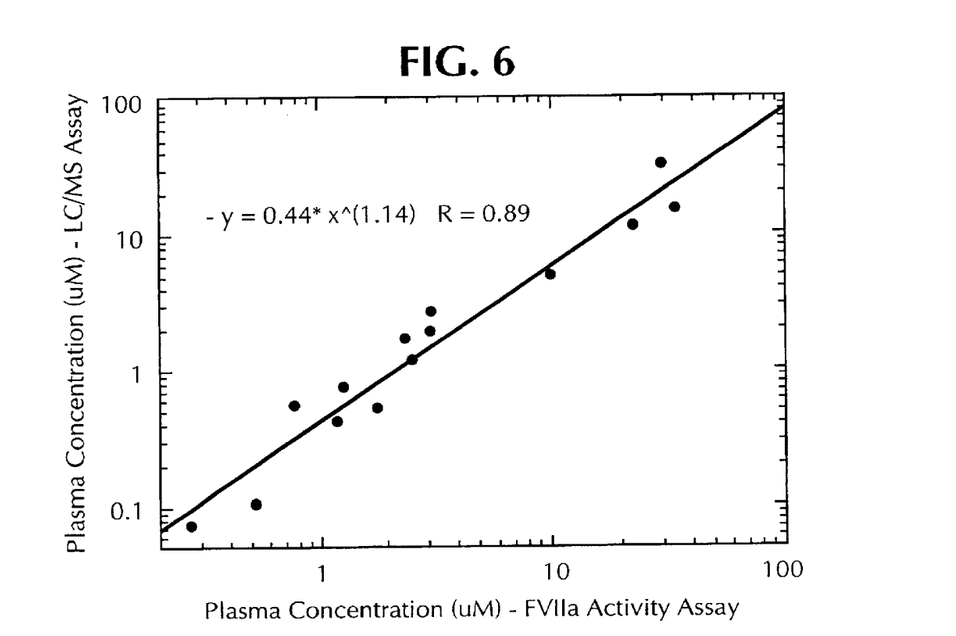
FIG. 6 is a graph showing the correlation of plasma concentration of a Factor VIIa inhibitor using the Factor VIIa activity assay of the present invention and the LC-MS/MS method.

The correlation of plasma concentration of 2-[6-(3-Carbamimidoyl-phenoxy)-3,5-difluoro-4-(1-methyl-3- phenyl-propylamino)-pyridin-2-yloxy]-5-dimethylamino-4-methyl-benzoic acid determined by FVIIa activity assay and LC-MS/MS method To validate the use of present FVIIa activity assay as a bio-marker, the plasma concentration of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid that was calculated based on FVIIa activity was compared with plasma concentration of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid that was measured by LC-MS/Ms method. There was a good correlative between the results obtained by two methods (see FIG. 5). It indicated that the plasma concentration of FVIIa inhibitors could be estimated based on the measurements of the FVIIa activity in plasma. In vitro and ex vivo study of 7-[(R)-3-(3-Amino-benzyl)-4-(4-amino-phenyl)-4-methyl-2,5-dioxo-imidazolidin-1-ylmethyl]-naphthalene-2-carboxamidine in hypercholesterolemic rabbit plasma Adding 7-[(R)-3-(3-Amino-benzyl)-4-(4-amino-phenyl)-4-methyl-2,5-dioxo-imidazolidin-1-ylmethyl]-naphthalene-2-carboxamidine between 0.008 and 1.5 µM to hypercholesterolemic rabbit plasma or Tris-buffer, the $IC_{50}$ standard curve was determined by means of $CH_3CN$ extraction from plasma sample or Tris-buffer. Like 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid, 7-[(R)-3-(3-Amino-benzyl)-4-(4-amino-phenyl)-4-methyl-2,5-dioxo-imidazolidin-1-ylmethyl]-naphthalene-2-carboxamidine showed a good recovery from $CH_3CN$ extraction (see FIG. 6).

Figure 7:
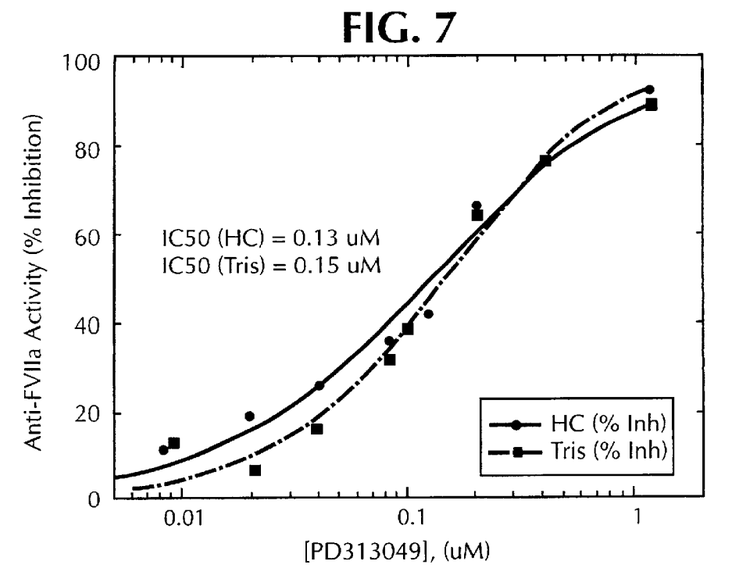
FIG. 7 is a graph showing recovery of 7-[(R)-3-(3-Amino-benzyl)-4-(4-amino-phenyl)-4-methyl-2,5-dioxo-imidazolidin-1-ylmethyl]-naphthalene-2 carboxamidine (PD 313049) in hypercholesterolemic rabbit plasma after $CH_3CN$ extraction.
Figure 8:
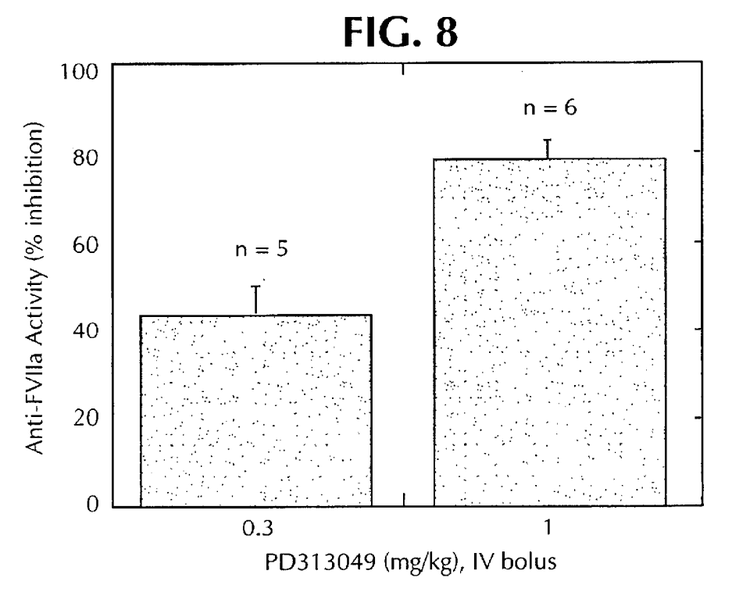
FIG. 8 illustrates the use of the method of present invention for the ex vivo determination of the biological activity of Factor VIIa following the administration of an inhibitor of Factor VIIa.

The inhibitory effect and plasma concentration of 7-[(R)-3-(3-Amino-benzyl)-4-(4-amino-phenyl)-4-methyl-2,5-dioxo-imidazolidin-1-ylmethyl]-naphthalene-2-carboxamidine was determined in balloon-induced injury model of thrombosis in hypercholesterolemic rabbits. The rabbits received two doses of the compound, IV bolus, 0.3 mg/kg (n=5) and 1.0 mg/kg (n=6). Blood samples were collected before and 3 minutes after administration of 7-[(R)-3-(3-Amino-benzyl)-4-(4-amino-phenyl)-4-methyl-2,5-dioxo-imidazolidin-1-ylmethyl]-naphthalene-2-carboxamidine. The results of in vivo efficacy will be reported separately (G. Gibson, R. Potoczak, et al., A new model of thrombosis in balloon injured femoral arteries of hypercholesterolemic rabbits. RR 741-00251). The inhibitory effect of 7-[(R)-3-(3-Amino-benzyl)-4-(4-amino-phenyl)-4-methyl-2,5-dioxo-imidazolidin-1-ylmethyl]-naphthalene-2-carboxamidine was measured by FVIIa activity assay. Plasma concentration of 7-[(R)-3-(3-Amino-benzyl)-4-(4-amino-phenyl)-4-methyl-2,5-dioxo-imidazolidin-1-ylmethyl]-naphthalene-2-carboxamidine was calculated based on the FVIIa activity in plasma. FIG. 7 and FIG. 8 are showing dose-dependent changes in inhibitory effect and plasma level of 7-[(R)-3-(3-Amino-benzyl)-4-(4-amino-phenyl)-4-methyl-2,5-dioxo-imidazolidin-1-ylmethyl]-naphthalene-2-carboxamidine.

Figure 9:
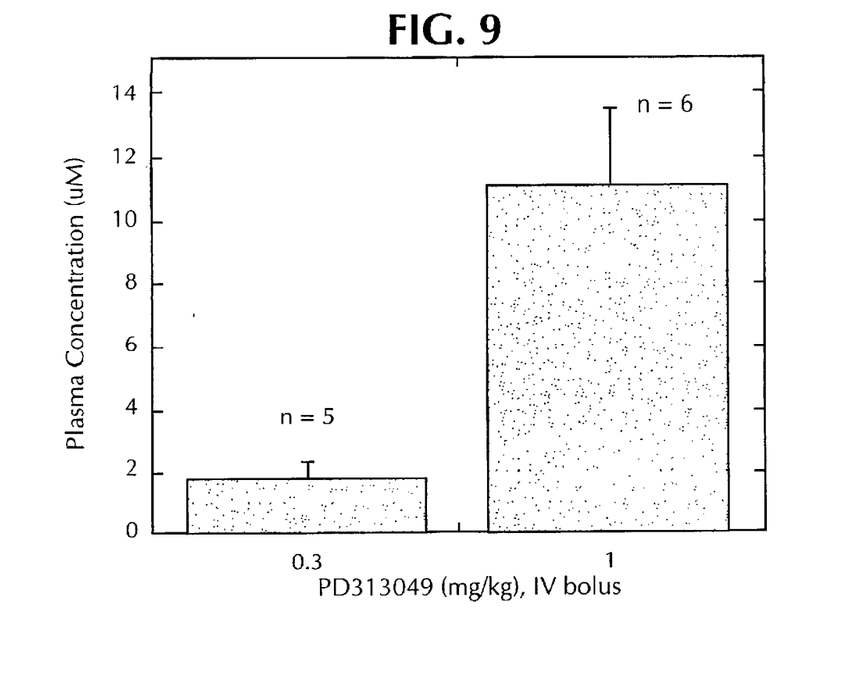
FIG. 9 shows the in vivo plasma concentration of a known Factor VIIa inhibitor calculated based on the ex vivo measurement of Factor VIIa activity in plasma.
Figure 10:
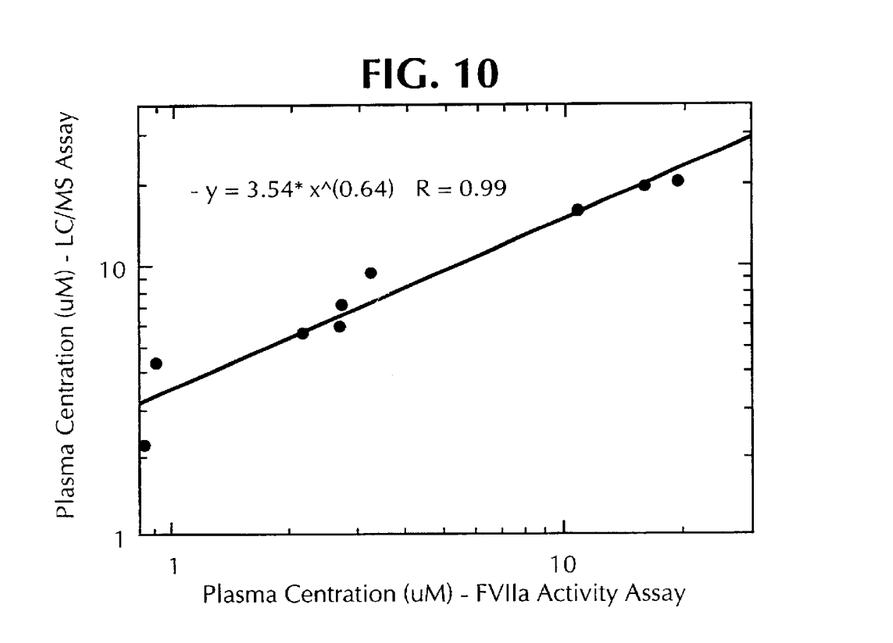
FIG. 10 illustrates the correlation of plasma concentration of a Factor VIIa inhibitor comparing the Factor VIIa activity assay of the present invention with the LC-MS/MS method.

The Correlation of Plasma Concentration of 7-[(R)-3-(3-Amino-benzyl)-4-(4-amino-phenyl)-4-methyl-2,5-dioxo-imidazolidin-1-ylmethyl]-naphthalene-2-carboxamidine Determined by FVIIa Activity Assay and LC-MS/MS Method Similar to the result of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid, there was a reasonable agreement between the plasma concentration of 7-[(R)-3-(3-Amino-benzyl)-4-(4-amino-phenyl)-4-methyl-2,5-dioxo-imidazolidin-1-ylmethyl]-naphthalene-2-carboxamidine measured by FVIIa activity assay and LC-MS/MS method (see FIG. 9).

EXAMPLE 2

Figure 11:
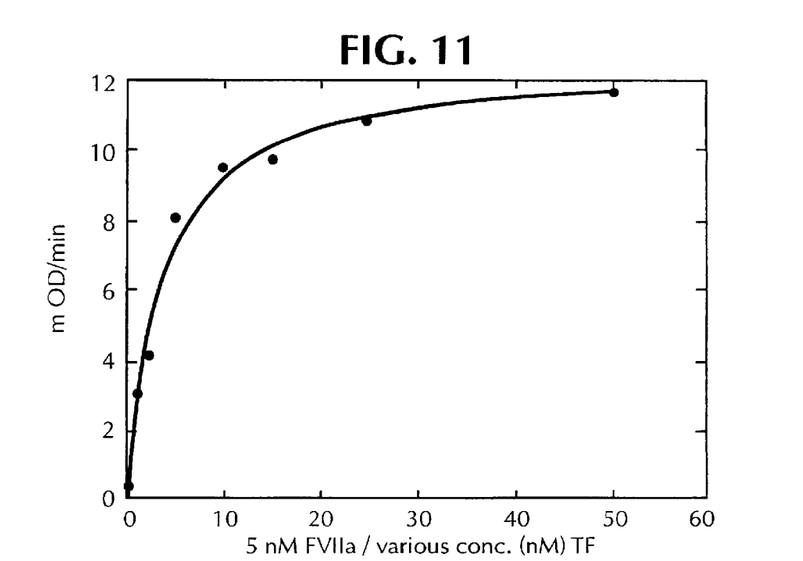
FIG. 11 is a graph illustrating the results of an experiment to determine the optimum concentration of TF in the present assay.

To determine the optimum concentration of TF in the assay, a series concentration of TF (0–50 nM) was evaluated for the optimal condition of FVIIa activity assay. This assay contained 5 nM FVIIa, 5 mM $CaCl_2$, 0.5 mM spectrozyme FVIIa, Tris-buffer that included 50 mM Tris, pH 7.4, 100 mM NaCl, and 0.1% BSA. Increasing concentrations of TF were added to the reaction mixture, and the reaction was monitored at 405 mm. The ratio of FVIIa/TF is approximately 1/1.5 to reach the maximal FVIIa activity as shown in FIG. 11.

EXAMPLE 3

In order to determine the optimum concentrations of Factor VIIa and plasma of the present assay, various concentrations of human plasma and FVIIa were be evaluated to the optimal condition of FVIIa activity assay. Various amounts of FVIIa were incubated with 15 nM TF at 37° C. in Tris-buffer containing human plasma, 5 mM $CaCl_2$, and 0.5 mM spectrozyme FVIIa. The reaction was monitored at 405 nm.

Figure 12:
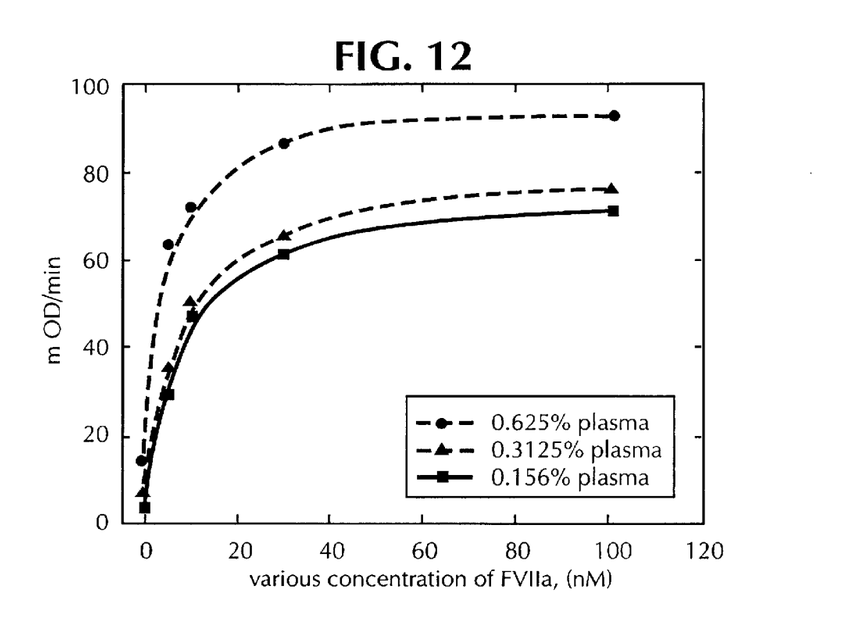
FIG. 12 is a graph illustrating the results of an experiment to determine the optimum concentration of Factor VIIa and plasma in the present assay.

The optimal condition of the FVIIa activity assay was found to include 0.625% plasma, 10 nM FVIIa, 15 nM TF, 5 mM $CaCl_2$, 0.5 mM spectrozyme FVIIa in final concentration as shown in FIG. 12.

EXAMPLE 4

Figure 13:
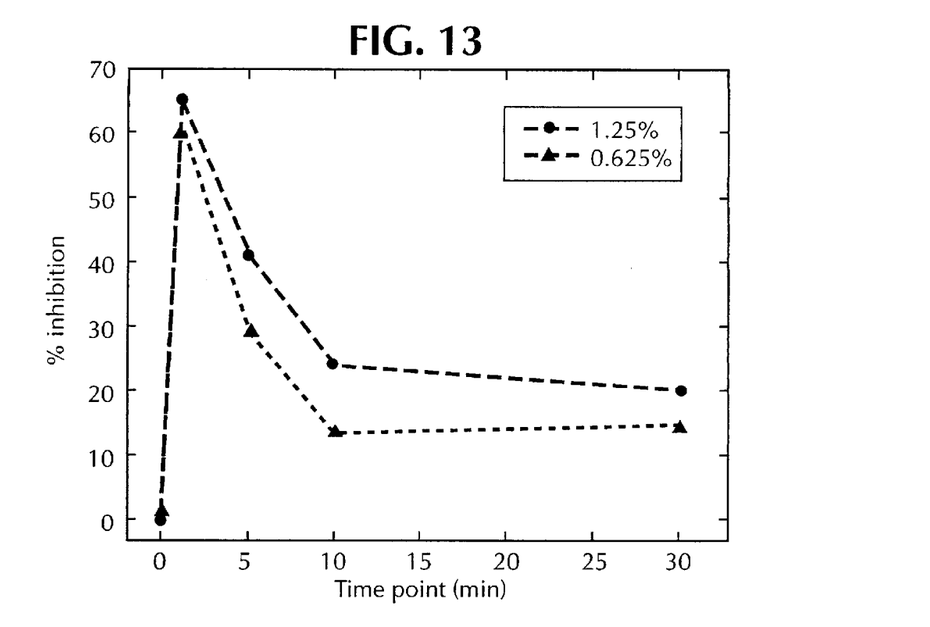
FIG. 13 is a graph showing the effects of using different plasma concentrations in the present assay.

In order to determine if different concentrations of plasma could be utilized in the present assay, plasma samples were collected from rabbits treated with 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid (3 mg/kg, IV bolus), a synthetic small molecular FVIIa inhibitor. The inhibition on FVIIa activity was investigated by two concentrations of plasma (1.25% and 0.625%) in the assay. The same inhibitory effect of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid on FVIIa activity was observed using 1.25% or 0.625% plasma samples in the assay as shown in FIG. 13. According to our data, this assay can be used with different concentrations of plasma to evaluate the inhibitory effect of FVIIa inhibitors.

EXAMPLE 5

Figure 4:
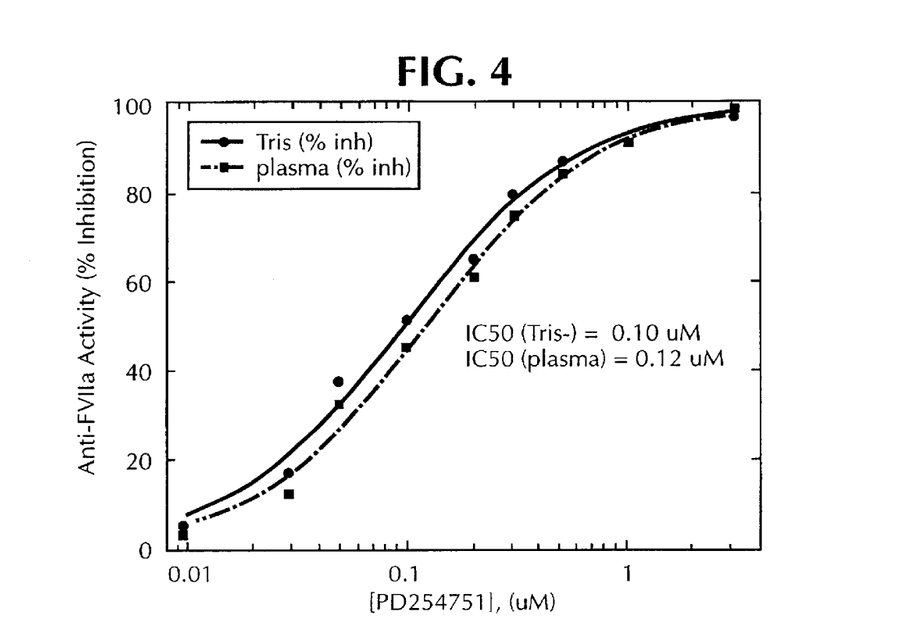
FIG. 4 shows the recovery of a Factor VIIa inhibitor added to rabbit plasma and extracted with $CH_3CN$ and then reconstituted in a Tris buffer.
Figure 14:
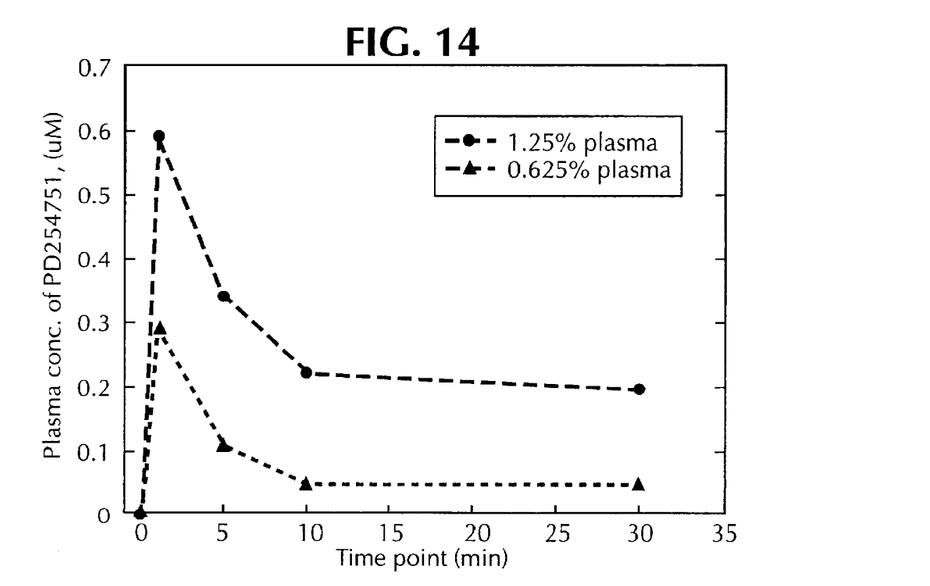
FIG. 14 is a graph showing the ex vivo study of 2-[6-(3-Carbamimidoyl-phenoxy)-3,5-difluoro-4-(1-methyl-phenyl-propylamino)-pyridin-2-yloxy]-5-dimethylamino-4-methyl-benzoic acid (PD 254751) in rabbit plasma.

In order to determine if plasma concentration of FVIIa inhibitors can be estimated based on the present FVIIa assay, the in vivo plasma concentration of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid was calculated based on ex vivo measurement of FVIIa activity in plasma. As shown in FIG. 4, 1.25% plasma samples indicated two-fold concentration of 2-[6-(3-Carbamimidoyl-phenoxy)-3,5-difluoro-4-(1-methyl-3-phenyl-propylamino)-pyridin-2-yloxy]-5-dimethylamino-4-methyl-benzoic acid compared with 0.625% plasma as shown in FIG. 14. The result shows that plasma concentration of FVIIa inhibitors can be estimated based on this FVIIa activity assay in various concentrations of plasma.

What is claimed is:

1. A method for measuring the activity of Factor VIIa in a plasma sample, said method comprising the steps of:

(a) combining a plasma sample with a solution comprising a buffer, Factor VIIa, tissue factor (TF), and a detectable Factor VIIa substrate; and (b) detecting the amount of the detectable substrate catalyzed to determine the activity of Factor VIIa in the sample.

2. A method according to claim 1, further comprising the steps of:

(c) combining a quantity of the plasma sample with acetonitrile; and (d) drying the plasma sample following step (a).

3. A method according to claim 1, wherein the detectable substrate comprises a chromogenic substrate.

4. A method according to claim 3, wherein the chromogenic substrate comprises a peptide element and a cleavable paranitroaniline element.

5. A method according to claim 1, wherein the buffer comprises Tris.

6. A method according to claim 5, wherein the solution comprises bovine. serum albumin.

7. A method according to claim 1, wherein the solution comprises $CaCl_2$.

8. A method according to claim 1, wherein the solution comprises plasma.

9. A method according to claim 2, wherein said drying step comprises subjecting the sample to a temperature of approximately 37° C.

10. A method according to claim 1, wherein the solution comprises Tris buffer, plasma, bovine serum albumin, Factor VIIa, tissue factor, $CaCl_2$, and detectable Factor VIIa substrate.

11. A method for determining whether a candidate compound inhibits Factor VIIa activity, said method comprising the steps of:

(a) administering to a subject a candidate compound;

(b) obtaining a plasma sample from the subject;

(c) combining the plasma sample with a solution comprising a buffer, Factor VIIa, and a detectable Factor VIIa substrate;

(d) measuring the Factor VIIa activity, wherein inhibited Factor VIIa activity, relative to a control not contacted with the candidate compound, indicates that the candidate compared inhibits Factor VIIa activity;

(e) combining a portion of the plasma sample with acetonitrile; and (f) drying the plasma sample following step (e).

12. A method according to claim 11, further comprising the steps of:

(g) combining a portion of the plasma sample with acetonitrile; and (h) drying the plasma sample following step (b).

13. A method according to claim 11, wherein step (d) further comprises measuring the amount of the detectable substrate catalyzed by Factor VIIa relative to the control, wherein less substrate catalyzed relative to the control indicates that the candidate compound inhibits Factor VIIa and no change in substrate catalyzed relative to the control indicates that the candidate compound does not inhibit Factor VIIa.

14. A method according to claim 11, wherein the detectable substrate comprises a chromogenic substrate.

15. A method according to claim 14, wherein the chromogenic substrate comprises a peptide element and a cleavable paranitroaniline element.

16. A method according to claim 11, wherein the buffer comprises Tris.

17. A method according to claim 11, wherein the solution comprises bovine serum albumin.

18. A method according to claim 11, wherein the solution comprises tissue factor.

19. A method according to claim 11, wherein the solution comprises $CaCl_2$.

20. A method according to claim 11, wherein the solution comprises plasma.

21. A method according to claim 11, wherein said drying step comprises subjecting the sample to a temperature of approximately 37° C.

22. A method according to claim 11, wherein the solution comprises Tris buffer, plasma, bovine serum albumin, Factor VIIa, tissue factor, $CaCl_2$, and detectable Factor VIIa substrate.

\* \* \* \* \*